United States Patent [19]
Newkome et al.

[11] Patent Number: 5,886,127
[45] Date of Patent: Mar. 23, 1999

[54] COMBINATORIAL METHOD OF FORMING CASCADE POLYMER SURFACES

[75] Inventors: George R. Newkome, Apollo Beach; Charles N. Moorefield, Tampa, both of Fla.

[73] Assignee: University of South Florida, Tampa, Fla.

[21] Appl. No.: 971,872

[22] Filed: Nov. 19, 1997

Related U.S. Application Data

[63] Continuation-in-part of Ser. No. 705,905, Aug. 28, 1996.
[51] Int. Cl.[6] .................................................. C08G 18/71
[52] U.S. Cl. ............................ 528/49; 525/440; 525/452; 525/474
[58] Field of Search ..................................... 525/440, 452, 525/474; 528/49

[56] References Cited

U.S. PATENT DOCUMENTS

| | | | |
|---|---|---|---|
| 5,154,853 | 10/1992 | Newkome et al. . | |
| 5,206,410 | 4/1993 | Nekome et al. . | |
| 5,610,268 | 3/1997 | Meyer | 528/363 |
| 5,663,260 | 9/1997 | Frechet | 526/309 |

OTHER PUBLICATIONS

Carell et al. (1995) New promise in combinatorial chemistry: synthesis, characterization, and screening of small–molecule libraries in solution. *Chem. Biol.*, 2:171:183.

Carell et al. (1994) A novel procedure for the synthesis of libraries containing small organic molecules. *Angew. Chem. Int. Ed. Engl.*, 33(2):2059–2061.

de Brabander–van den Berg and Meijer (1993) Poly(propylene imine) dendrimers: large–scale synthesis by hetereogeneously catalyzed hydrogenations. *Angew. Chem. Int. Ed. Engl.*, 32:1308–1311.

Dominguez et al. (1961) Simple preparation of a very active raney nickel catalyst. *J. Org. Chem.*, 26:1625.

Gitsov and Frechet (1996) Stimuli–responsive hybrid macromolecules: novel amphiphilic star copolymers with dendritic groups at the periphery. *J. Org. Chem.*, 118:3785–3786.

Gitsov and Frechet (1993) Solution and solid–state properties of hybrid linear–dendritic block copolymers. *Macromolecules*, 26:6536–6546.

Newkome and Weis (1996) Di–tert–Butyl 4–[2–tert–Butoxycarbonyl)Ethyl]–4–Aminoheptanedicarboxylate. *Org. Prep. Proc. Int.*, 28:485–488 (only copy available).

Plattner et al. (1972) Synthesis of some DE and CDE ring analogs of camptothecin. *J. Am. Chem. Soc.*, 94:8613–8615.

vanGenderen et al. (1994) Observing individual generations in poly(propyleneimine) dendrimers with natural abundance $^{15}$N–NMR spectroscopy. *Recl.Trav. Chim. Pays–Bas.*, 113:573–574.

Worner and Mulhaupt 91993) Polynitrile–and polyamine–functional poly(trimethylene imine) dendrimers. *Angew Chem. Int. Engl.*, 32(9):1306–1308.

Xiang et al. (1995) A combinatorial approach to materials discovery. *Science*, 268:1738–1740.

*Primary Examiner*—Rachel Gorr
*Attorney, Agent, or Firm*—Kohn & Associates

[57] ABSTRACT

The method of forming a surface layer on a substrate is accomplished by dendrimerizing a mixture of branched monomers on the substrate surface wherein the monomers introduce heterogeneous functionalized branches and homogenous connectivity to the substrate. A cascade polymer coated substrate is formed consisting essentially of a substrate including a surface and at least one dendrimerized surface layer consisting of heterogeneous functionalities the layer being linked to the substrate by homogenous linkages, preferably isocyanate linkages.

3 Claims, 10 Drawing Sheets

COMBINATORIAL METHOD OF FORMING CASCADE POLYMER SURFACES

This application is a continuation-in-part of copending application Ser. No. 08/705,905 filed on Aug. 28, 1996. +gi

GRANT REFERENCE

The research carried out in connection with this invention was supported in part by a grant from the National Science Foundation, grant number DMR-92-17331.

TECHNICAL FIELD

The present invention relates to highly branched molecules possessing a three dimensional morphology. More specifically, the present invention relates to cascade polymers as molecules per se or as surfaces applied to various substrates. Such molecules and substrates possess uses in areas such as detergents, radio imaging, binding sites for drug delivery, polyfunctional basis and other areas of use.

BACKGROUND OF THE INVENTION

U.S. Pat. No. 5,703,271, filed Apr. 2, 1996, discloses a method of synthesizing multi-tier cascade polymers, as well as coating substrate surfaces, utilizing a novel family of stable trifunctionalized isocyanates. Continuing with applicants' previous work utilizing dendrimeric monomer building blocks to construct cascade polymers of predetermined internal and external architecture, applicants have begun to realize and further materialize some of the potential uses of the novel isocyanate building blocks. Previous work by applicants in forming cascade polymers were limited to the coupling of an acid (dendritic termini) and an amine. In an effort to bypass this relatively limited combination, applicants demonstrated the facile conversion of unique, sterically protected "Behera's amine" to the corresponding isocyanate by its treatment with triphogene (commercially available from Aldrich Chemical Co., catalog #33,075.2, referred to as "bis(trichloromethyl)carbonate") in the presence of triethylamine [Newkome and Weis, 1996].

The isocyanate monomers are excellent building blocks or modules for use in the transformation and introduction of surface functionality on either a cascade polymer under construction or on surfaces of substrates in general. The isocyanate based monomers also provide for rapid, iterative tier construction. That is, the layering of tiers or layers over a surface or about an existing cascade polymer can be performed relatively rapidly using the isocyanate monomers. Preliminary evaluations by applicants have demonstrated the facile reaction of Behera's isocyanate with generations 2 through 5 (8, 16, 32, 64 termini, respectively) of amine terminated, poly(propylene imine) dendrimers [Wörner, and Mülhaupt, 1993; deBrabander-van den Berg and Meijer, 1993] using tert-butyl alcohol as solvent. In this case, the reaction of Behera's amine isocyate building block with the poly(propylene imino) dendrimers constitutes the formation of a new dendrimer, using the dendrimers prepared as described by Wörner, and Mülhaupt, as the starting core. This confirms the potential of the monomer to react with nucleophilic groups, as well as affords a reasonable insight into the reacting potential for other hindered isocyanate building blocks. Stoichiometric reactions result in the isolation of pure (95% or greater) surface modified dendrimer with no by-products. These materials can be sequentially deprotected and subjected to farther elaboration.

In view of the above, there is significant demonstration that the isocyanate based building blocks can be employed to "dendrimerize" any common material(s) possessing an acidic proton(s) or nucleophilic site(s). Examples of such substrates include silica based substances, functionalized classical linear polymers, functionalized classical micelles, microgels, spherical polymers and, as demonstrated via reaction with the poly(propylene imine dendrimers, cascade polymers. Such surface coatings or films are useful for the creation of thermally and chemically stable coatings. Thus, these coatings can be used as protective coatings on clothing, other fabrics, metal surfaces, composite-based materials, semiconducting materials or the like. Surface property modification, such as wetability, is also possible.

Biological molecules are often identified by the synthesis and screening of large collections (termed "libraries") of structures. Such methods are commonly employed with the humoral immune system, which can generate and screen some $10^{12}$ antibody molecules to identify one that specifically recognizes and binds a foreign pathogen. The development of catalytic antibodies was one of the first applications of such molecular libraries to chemistry. Other such methods have been further developed for generating and screening large populations of biological molecules in vitro for binding, catalysts or both. A large effort has been devoted towards the application of these "combinatorial libraries". Such libraries are generated by combining large numbers of precursors.

The present invention relates to the further advancement of the use of monomers normally employed in the preparation of cascade polymers and more specifically to stable multifunctionalized isocyanates in combination with combinatorial chemistry to provide novel surface layers on substrates. That is, the potential to create and utilize new materials prepared "combinatorially" is exploited by the present invention. An advancement in cascade polymer dendrimeric chemistry is derived wherein combinatorial [Xiang et al., 1995] methods of dendritic construction utilize monomer mixtures possessing varying compositions of differing monomers (preferably isocyanate based monomers) for sequential tier formation.

SUMMARY OF THE INVENTION

In accordance with the present invention, there is provided a method of forming a surface layer on a substrate by attaching a mixture of branched monomers on the substrate wherein the monomers have heterogenously functionalized branches and homogenous connectivity to the substrate.

The present invention further provides a cascade polymer coated molecule consisting essentially of a substrate including a surface and at least one dendrimerized layer consisting of heterogeneous functionalities, the layer being linked to the substrate by homogenous linkages.

DETAILED DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

The present invention provides a cascade polymer coated molecule and a method of forming the same. The method generally includes the steps of dendrimerizing a mixture of branched monomers on a substrate wherein the monomers have heterogenously functionalized branches and homogenous connectivity to the substrate.

The term "substrate" is defined more particularly in the background art section of the present application and is used generally herein. The substrate can be a core molecule, such as found in classic, small, carbon-based molecules possessing nucleophiles such as nitrogen, or an extended cascade polymer having a surface area which is then dendrimerized in accordance with the present inventive method. Such cascade polymers, in the forms of unimolecular micelles, are disclosed in detail in U.S. Pat. Nos. 5,154,853 and 5,206,410, both to applicants of the present invention. Examples of such substrates are silica based substances, functionalized classical linear polymers, functionalized classical micelles, microgels, spherical polymers, as well as multifunctionalized or monofunctionalized inorganic and organic molecules. Examples of such molecules are polysiloxanes, polysaccharides, and the like. Most generally, the present invention can be employed to "dendrimerize" any common material(s) possessing an acidic proton(s).

The term "dendrimerizing" or "dendrimerize" relates to the application, in a tier or layering type manner, of monomers which chemically bond to reactive surface groups. As stated above, the common denominator that related the reactive surface groups on the substrate surface is that the reactive groups include an acidic proton. Thus, the dendrimerizing step characterizing the present invention involves the attachment of at least one monomer layer, or several monomer layers, over a reactive surface. The reactive surface can thus be said to be dendrimerizing. Since nucleophilic functional groups can be found on most common materials, the present invention has broad application as a means of coating or forming a surface layer on a wide variety of substrates. Since the monomer utilized with the present invention can have a wide range of functionalities, as described in the co-pending patent application, U.S. Ser. No. 08/626,395, as previously cited, the present invention can have a wide range of utilities by imparting a wide range of desired properties to a surface of a wide range of substrates. In other words, the scope of utility of the present invention is enormous.

As stated above, the inventive method is characterized by the step of dendrimerizing a mixture of branched monomers on a substrate. Preferably the branched monomers are multifunctional (preferably trifunctionalized) possessing stable isocyanate moieties. Such isocyanates are described in detail in the copending patent application, U.S. Ser. No. 08/626, 395, cited above. Chemically, such isocyanates can be characterized by the formula $$O{=}C{=}N{-}C(CH_2{-}R)_3$$

with R being selected from the group including:
a) —CH$_2$—CH$_2$—COOR'
b) —O—CH$_2$—CH$_2$—COOR',
c) —O—CH$_2$—CH$_2$—CN, or
d) —CH$_2$—CH$_2$—O—R"

with R" being selected from the group consisting of alkyl, cycloalkyl, aryl heteroaryl ester functionality, and sulfur or a silicon atom bearing substituents selected from the group including:

wherein R'" is alkyl (C-1 to C-20), cycloalkyl (C3–C-10), aryl, aralalkyl, heteroaryl, polycycloalkyl, and adamantyl. This formula is only exemplary of the isocyanates and is not intended limit the broad scope of multifunctionalize isocyanates capable of use in accordance with the present invention.

In utilizing the combinatorial chemistry approach, the present invention is characterized by the step of dendrimerizing the mixture of branched monomers on the substrate wherein the monomers have heterogeneous functionalized branches and homogenous connectivity to the substrate. The monomers which are dendrimerized to the surface layer of the substrate are not a homogenous batch having a single functionality but rather a mixture of different monomers having different functionalized branches. Some of the monomers may have carboxyl termini, some of the branches may have alcohol termini, some of the branches may have ester termini, etc. Hence, the resulting coated substrate possesses a cascade polymer coating consisting essentially of the substrate surface having at least one dendrimerized surface layer consisting of heterogeneous functionalities, the layer being linked to the substrate by a series of homogenous linkages. By using the preferred isocyanate building blocks, the homogenous linkages are of the formula where Nu=Nucleophile. Thus, the application of the present invention utilizes the combinatorial method of dendritic construction by using building block mixtures possessing various compositions of different isocyanate based monomers for sequential tier formation. The present invention can be utilized to form a single surface layer or multiple tiers in a cascade polymer type expansion. The present invention can be termed "combinatorial expansion chemistry" as the combinatorial chemistry is utilized in an ever expanding layering or tier formation. With further tier formation, the functionalization of the surface densities because of the multiplicity of the dendrimeric process.

In the process of the present invention, identical mixtures consisting of the same monomer composition can be used at each tier or the composition can be varied. Also, combinatorial tier growth can be employed in concert with standard tier construction whereby a unit compositional tier is added.

The combinatorial chemistry approach thereby provides a mixture of surface functionalities. This mixture of surface functionalities is reflective of the ratio of the mixture of branched monomers utilized in the dendrimerizing step of the present invention. That is, during the dendrimerizing step, the substrate is reacted with the mixture of monomers having a predetermined ratio of component functionalities. The dendrimerized surface is formed and includes a layer of monomers consisting of a mixture of functionalities of the same predetermined ratio as that of the mixture of monomers having been reacted. Hence, the nature of the functionalities on any given surface can be predetermined by the formation of the mixture of monomers used to form that layer.

More specifically, the dendrimerizing step can be further defined as reacting the monomer mixture with the substrate surface wherein the monomer mixture consists of compounds of the formula OCN-☐ wherein -☐ is a mixture of protected functionalities, at least some of the protected functionalities possessing complementary protective groups.

linkage is formed between the substrate surface and each of the monomers. The complementary protected groups are then deprotected resulting in a heterogeneous surface layer reflecting the heterogeneous mixture of the deprotected functionalities. Accordingly, the combinatorial tier construction of the present invention employs complementary protection and deprotection strategies at the same stage of molecular growth. This is in contrast to prior art methods which result from traditional protection-deprotection generational manipulation. The present invention derives from tier construction using a mixture (of any desired composition) of functionally compatible monomers in similar monomer connectivity, preferably isocyanate based.

With regard to the terms used above, the term "protected functionalities" is used in its common chemical sense. That is, during the iterative process, the functionalities which terminate the branches of the monomer must be protected during the iterative process to prevent their untimely reactivity. When further branching or tiering is desired or if exposure of the functionalities is desired, the branches are then deprotected by means well known in the art so as to expose the functionalities. One permutation of the present invention utilizes functionalities on different monomers which are all complementary such that all of the protected groups can be deprotected. An alternative embodiment, exemplified below, is where some of the functionalities are not complementary and thereby not deprotected. As used herein, "complementary" is used in its known connotation, referring to protection or protection groups "logically" chosen on different monomers in the same reaction. When deprotection of one or more is desired, the logically chosen other protective groups will not interfere or be affected. In this manner, further tier formation will extend from the deprotected branches but not from the protected branches. Thus, internal functionalities can be created on shorter branched arms which were protected and remain protected during the iterative process but can be deprotected, if desired, at a later step.

Figure 1A:
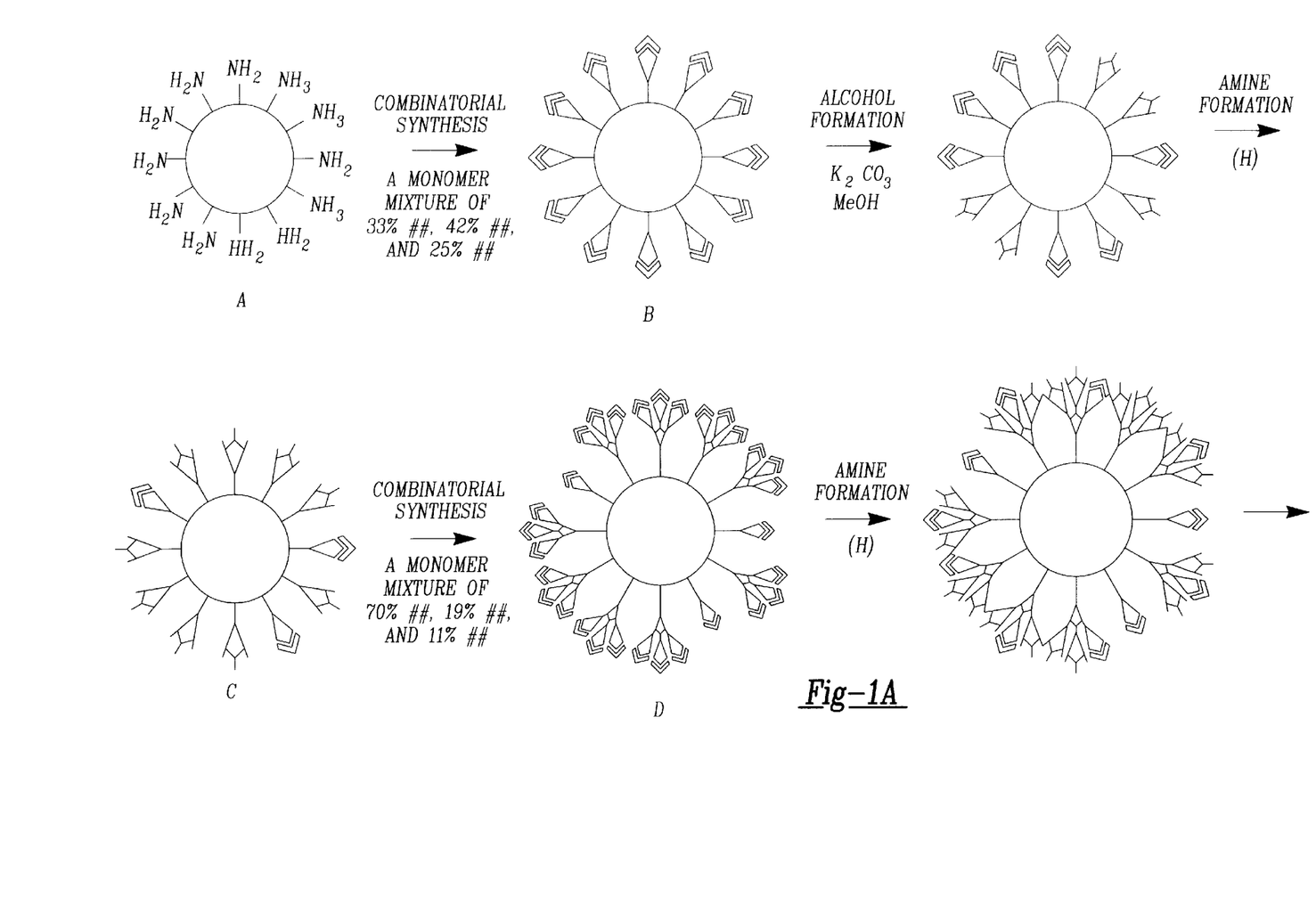
FIG. 1 is a schematic representation of combinatorial based dendritic construction of dendrimers made in accordance with the present invention.
Figure 1B:
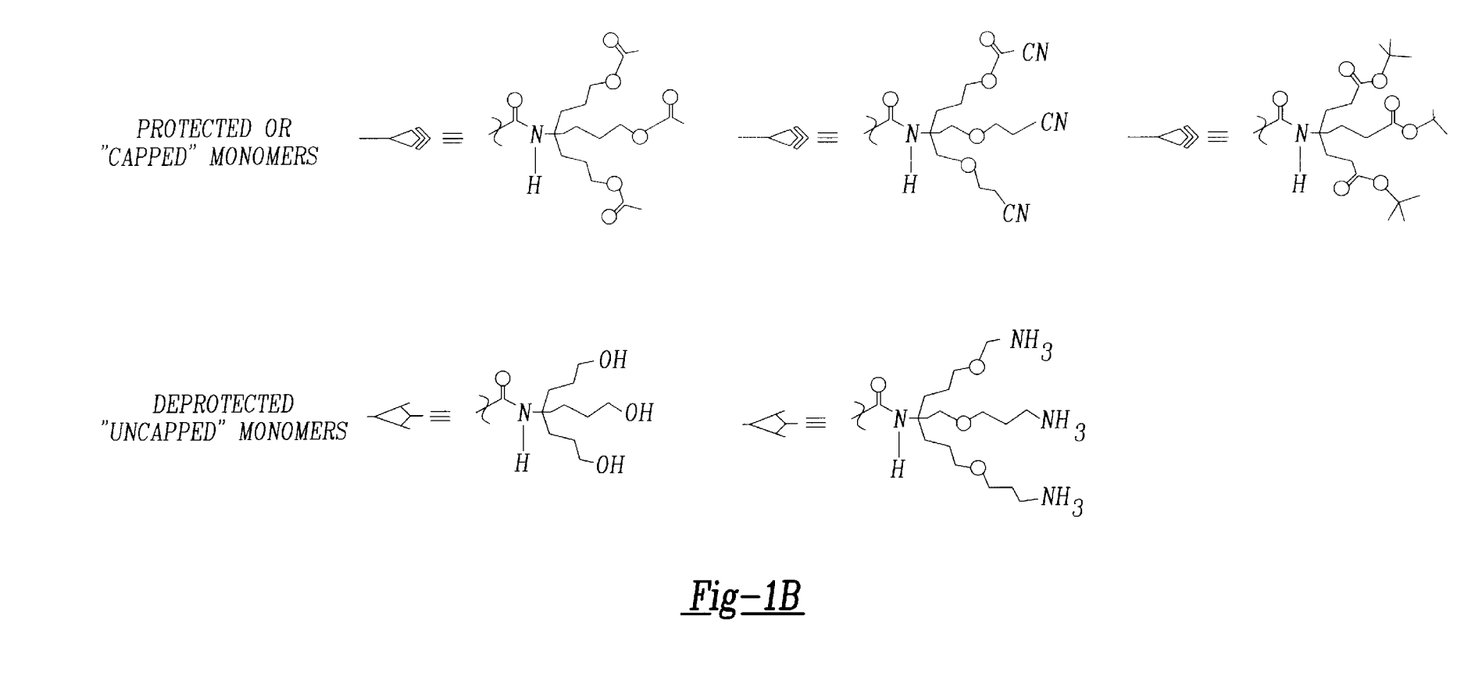

FIG. 1 illustrates one permutation or embodiment of the combinatorial process of the present invention. "Diversified" surface functionalization and tier construction using a generic dodecaamine dendrimer(1) is affected by treatment with a "stoichiometrically correct" mixture of three different isocyanate monomers possessing complementary protective groups. In this example, the mixture consists of This reaction results in dendrimers, as exemplified by compound 2 in FIG. 1, possessing a new generation or layer with a surface composition similar to the monomer mixture composition. Subjection of the multifunctional dendrimers derived thereby to basic transesterification [Plattner et al.] utilizing potassium carbonate and ethanol, and reduction utilizing Raney nickel [van Gendersen, 1994; Domingeuz et al., 1961] or cobalt [Wörner, and Mülhaupt, 1993; deBrabander-van den Berg and Meijer, 1993 will sequentially deprotect the alcohol and amine termini leaving the masked carboxylic acids intact to afford the poly (aminoalcohol), compound 3, in FIG. 1. Repetition of this combinatorial procedure, using different composition mixtures of isocyanate monomers, yields second generation multicomponent dendrimers such as dendrimer 4 in FIG. 1.

Figure 2:
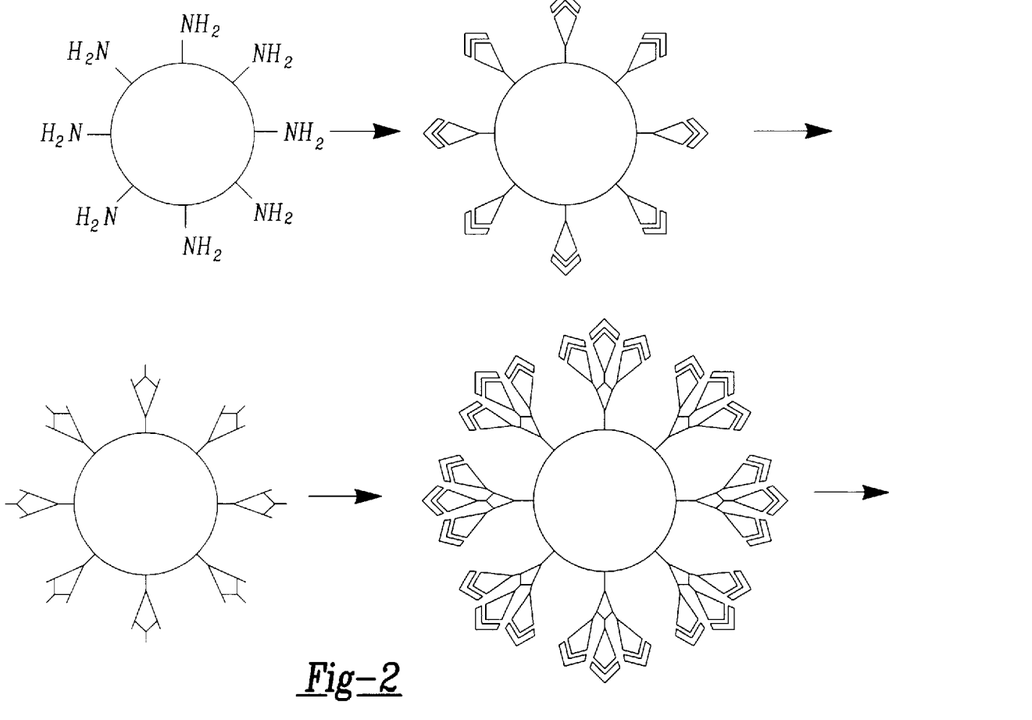
FIG. 2 is a schematic representation of hydrolytic, combinatorial based, dendritic materials made in accordance with the present invention.

The combinatorial procedure is well suited to superstructure property and architectural modification of dendrimers and appropriate functionalized materials. Thus, distinctive void regions or cavities can be crafted into the branched framework that can be employed for such processes as guest molecule hydrolysis reactions provided that appropriate hydrolytic functionality has been incorporated at or near the cavity. Rapid construction and screening of materials with varying compositions follow protocols very similar to that currently employed for small molecule library (usually pharmaceutical) screening [Carell et al., 1994 and 1995], although hydrolytic processes are exploited such as shown as dendrimer 5 in FIG. 2.

The combinational material has the potential to effect dendrimer properties in completely unexpected ways. This is accomplished by surface modification of a homogenous surface into a heterogenous macromolecule termed a "heterodendrimer". The term connotes an unsymmetrical dendrimer (14 in FIG. 6) having a multifarious surface. The surface can have diverse functionality as well as individually diverse characteristics. That is, the termini have a heterogenous distribution of terminal groups.

As shown in Example 4, herein, such heterodendrimers can possess unexpected properties. The polyamine dendrimer afforded by liberation of the amine moieties on dendrimer 13 shown in FIG. 6 displays amphiphitic behavior. In a biphasic system, if for example methanol and water and $CHCl_3$, the heterodendrimer showed at least some solubility in both phases. This exemplified the ability of flexible broad arms of the dendrimer to extend and rotate soluble moieties into solution while retracting less or insoluble moieties into the molecular superstructure.

By altering the ratio and nature of function groups at the termine the behavior of the heterodendrimer can be engineered to the desired modifications. For example, a heterodendrimer with a 75:25 mixture of surface amine and benzyl groups is completely miscible in water and insoluble in $CHCl_3$: while a heterodendrimer possessing a surface coat with a 25:75 mixture of amine and benzyl groups reverses the solubility.

Envisioned uses for such engineered and tailored materials include the ability to incorporate new additives for property modification (such as toughness, hardness, oxidation resistance, and flexibility) of water-based and hydrocarbon-based coatings. These materials can also be employed as additives for plastics, resins, glasses, fibers, and composite-based materials. Since the combinatorial method provides for the miscibility and solubility of substrates in the full spectrum of liquid environments, from aqueous to hydrocarbon, substrates that are capable of guest encapsulations can be considered to be 'universal micelles'. It is further envisioned that the gas, liquid, and solid diffisional characteristics of common materials such as plastics can be altered via the incorporation of combinatorial-based materials.

In view of the above, a cascade polymer coated molecule can be constructed consisting essentially of a substrate including a surface and at least one dendrimerized surface layer consisting of heterogeneous functionalities, the surface layer being linked to the substrate by homogenous linkages. Preferably, at least some of the functionalities are depro-tected and linked to the substrate by linkage of the formula The substrate surface can include functional groups selected from the group derived from stable trifunctionalized isocyanates. The groups can consist of aryl, alkyl and aralalkyl alcohols, carboxyls, esters, and other reactive groups possessing an acidic proton.

The present invention possesses utility in various area of surface coating and polymer production. For exarnple, the present inventive synthesis can be used to derive protective coatings, such as hydrophilic coatings for fabrics such as filters, hospital gowns, operative curtains, and the like. By controlling the functionalized termini of the monomers, various levels of hydrophobicity can be obtained on a functionalized surface made in accordance with the present invention. Hence, wetting of surfaces can be controlled so as to form super wet or super dry materials. Likewise, protective coatings can be formed having heterogeneous functionalities thereon. Hence, as disclosed in U.S. Pat. No. 5,650,101, heterogeneous functionalities can be incorporated into or onto surfaces having various catalytic sites therein. Thereby, a series of reactions can be accomplished on the surface of a molecule.

EXPERIMENTAL EXAMPLES

Example 1

Figure 3:
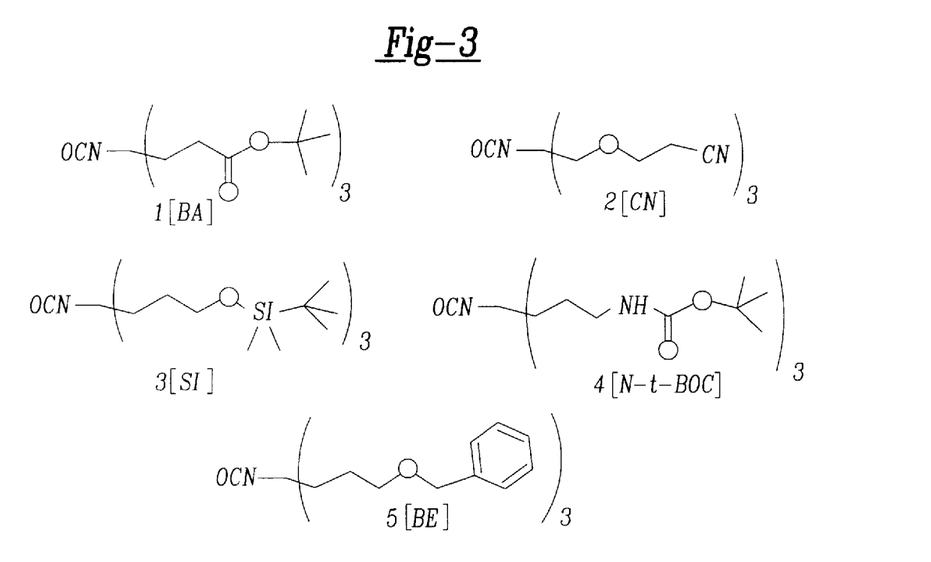
FIG. 3 shows examples of alkyl isocyanates based, dendritic building blocks.
Figure 4A:
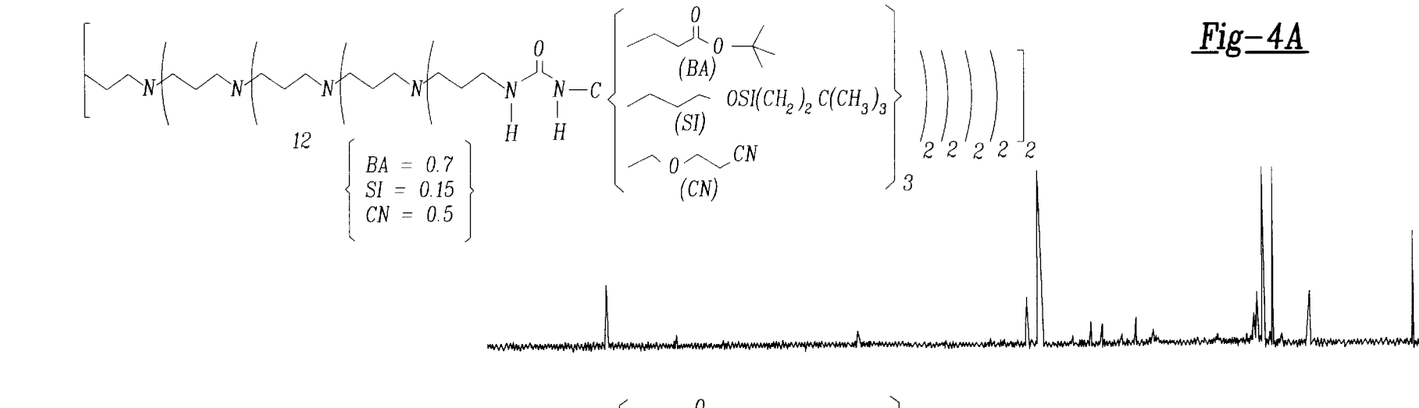
FIG. 4 shows comparison of $^{13}$C NMR spectra for ester, cyano, and siloxane homo-surfaced dendrimers and the corresponding first layer combinatorial-based dendrimers.
Figure 4B:
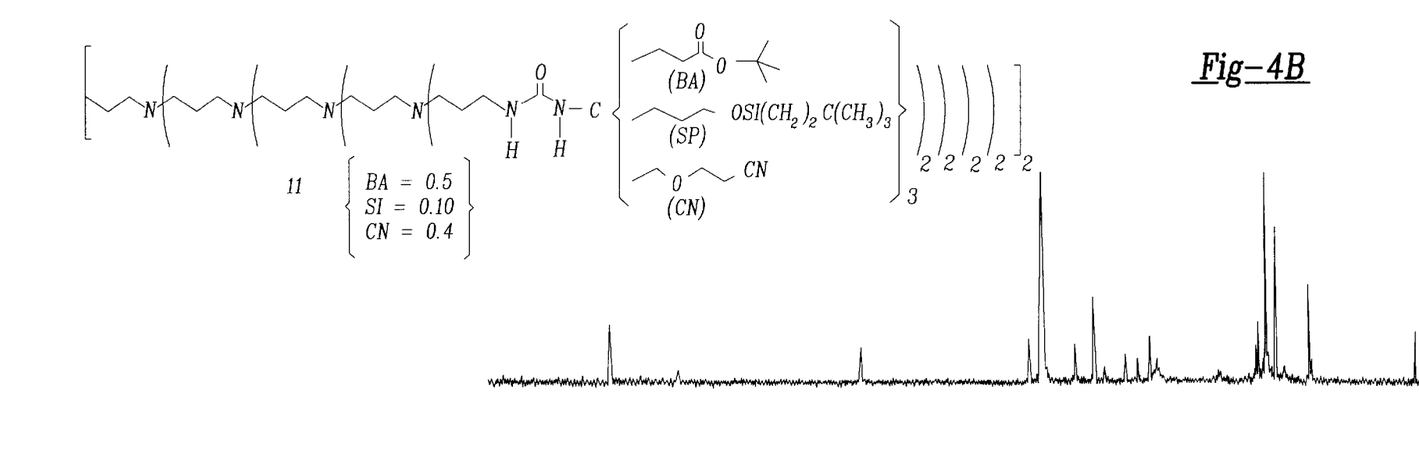
Figure 4C:
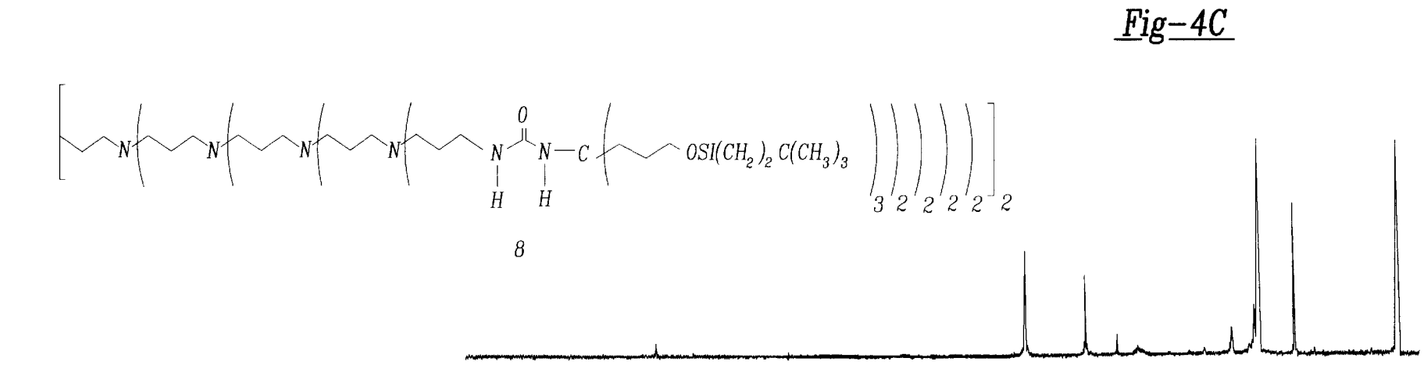
Figure 4D:
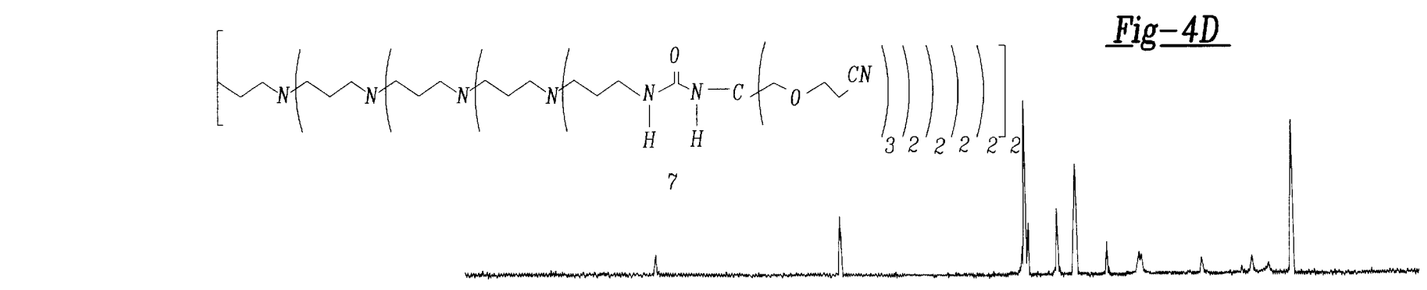
Figures 4E, 4F:
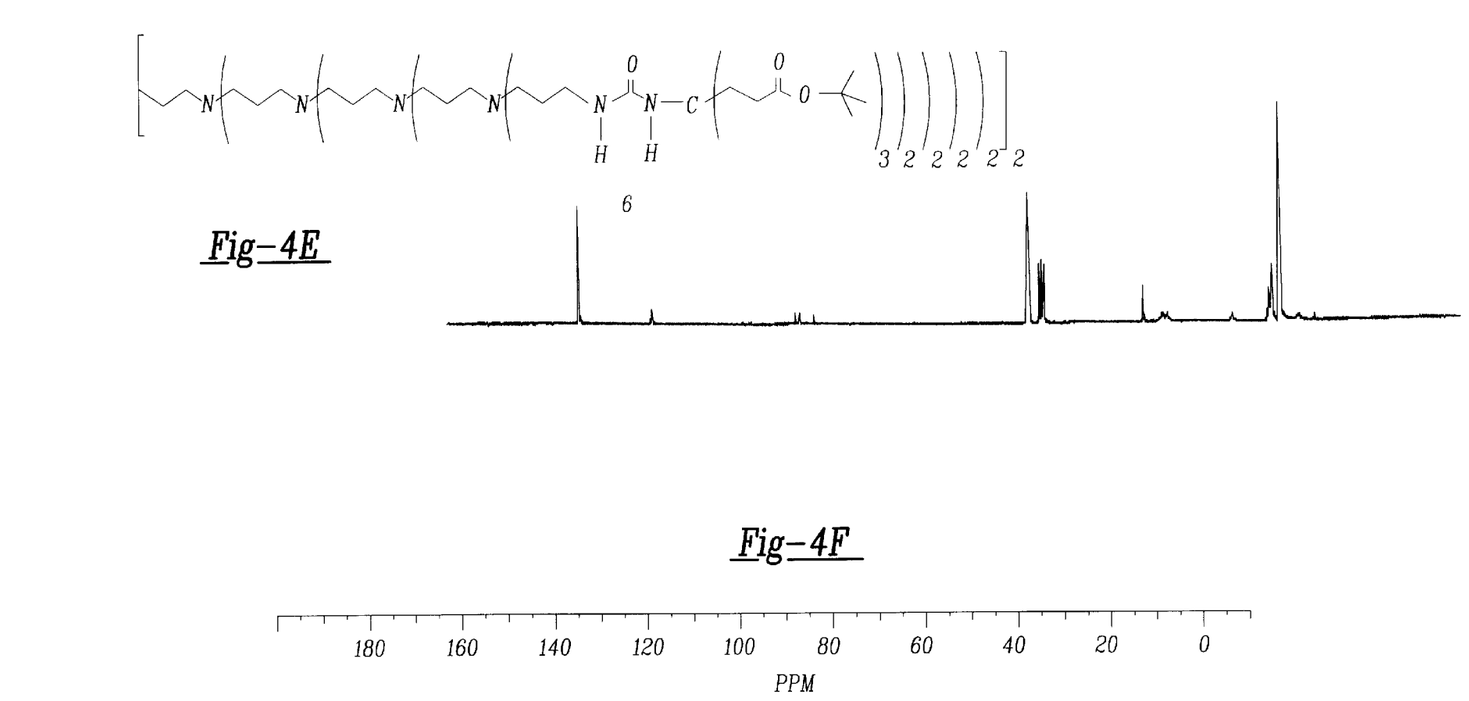
Figure 5A:
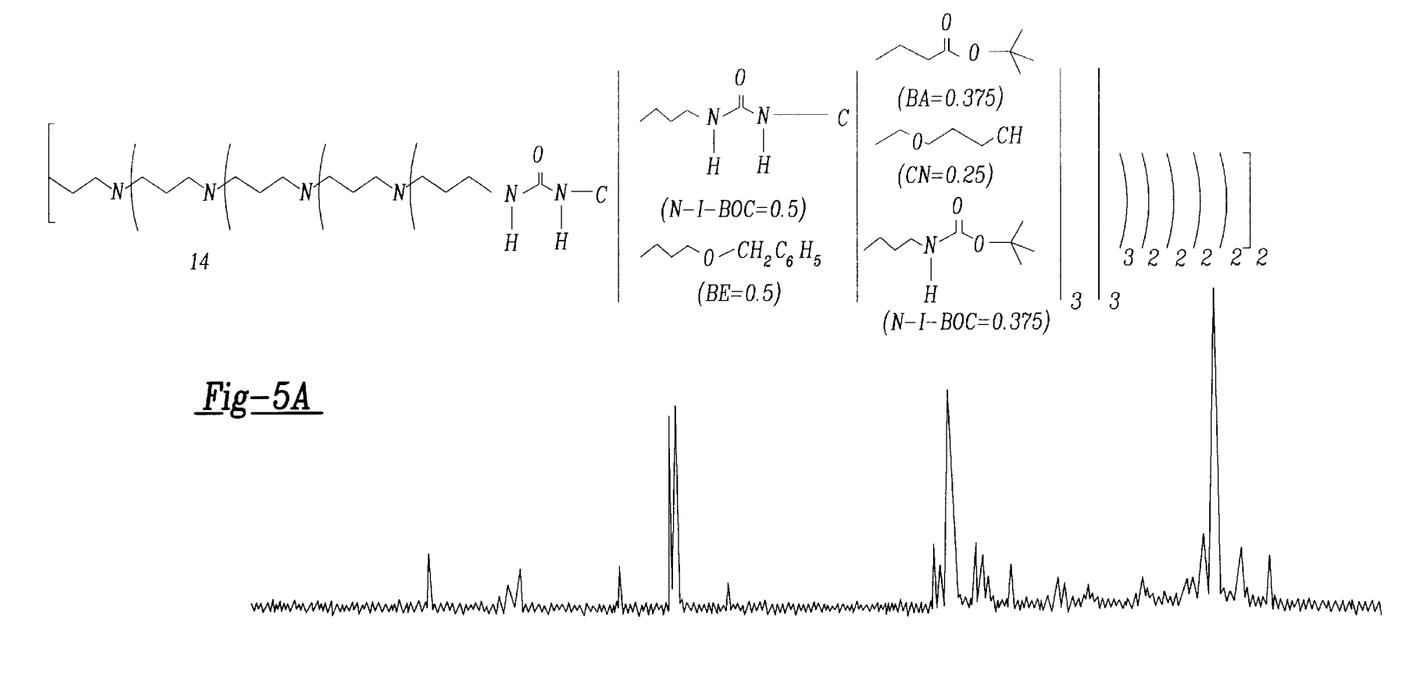
FIG. 5 shows a comparison of $^{13}$C NMR spectra of a carbamate and benzyl ether-coated dendrimers with the corresponding first layer material and unique second layer denrimers.
Figures 5B, 5E:
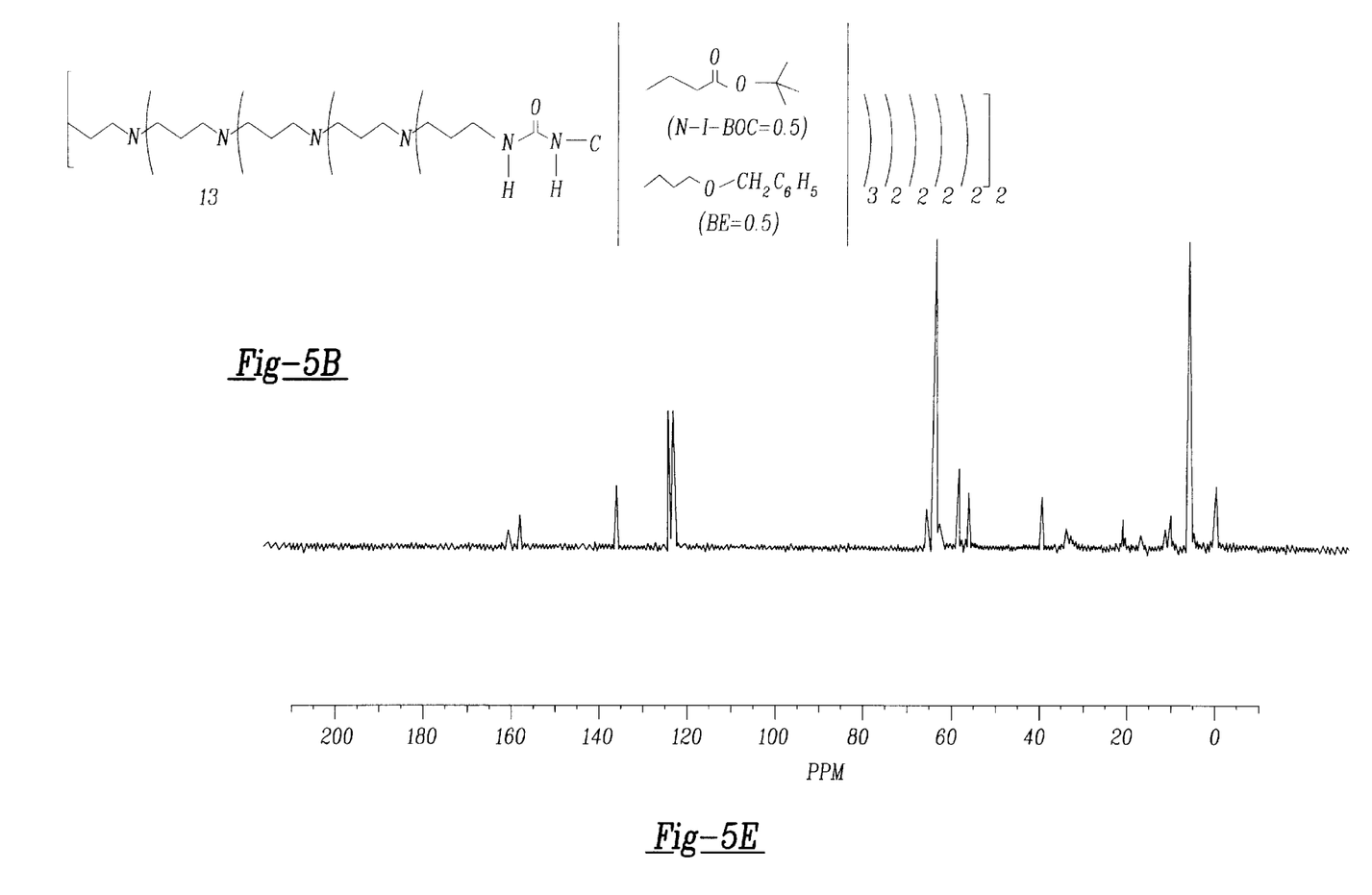
Figure 5C:
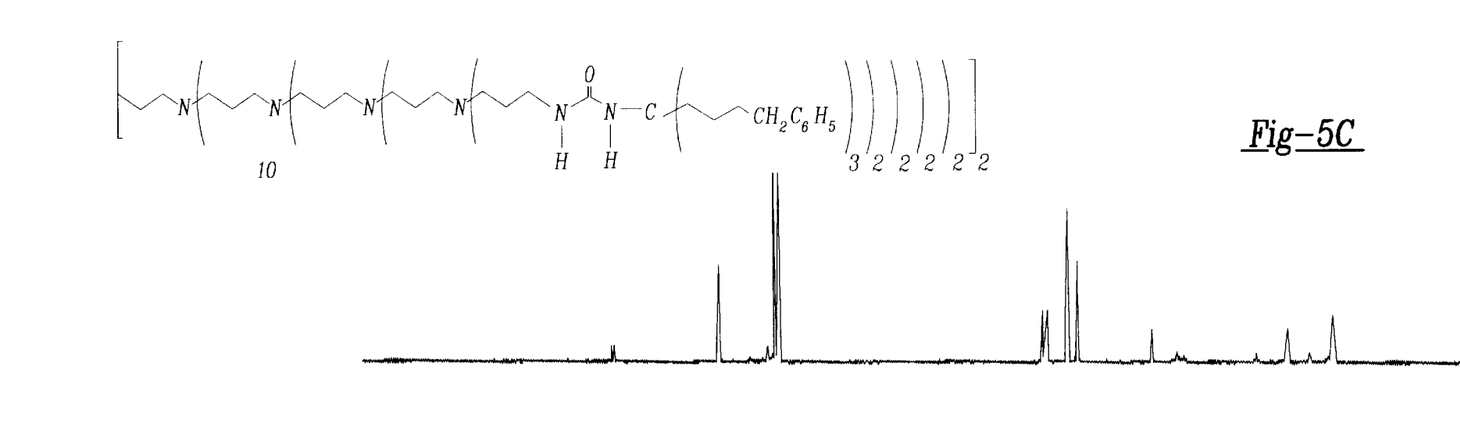
Figure 5D:
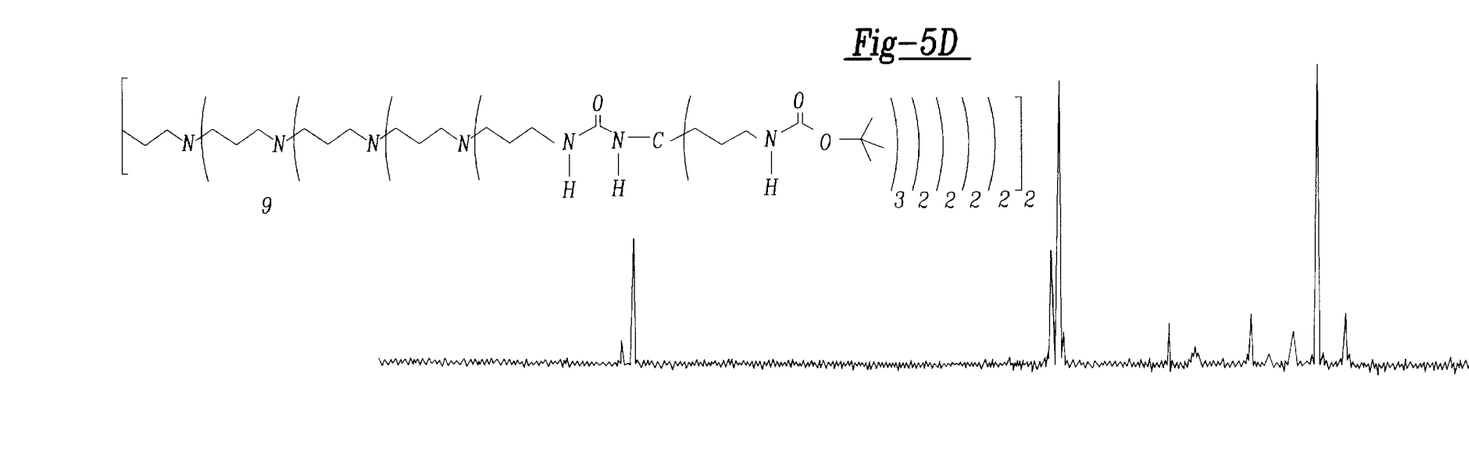

Individual reaction of the isocyanate monomers (1–5, as shown in FIG. 3, with the fourth tier, 32-amine terminated poly(propylene imine) dendrimer De Brabander-van den Berg and Meijer, 1993; Wörner, and Mülhaupt, 1993] (DSM 32 PPI) in refluxing tert-BuOH or dichloromethane afforded (>90%) the corresponding 96 ester (6), cyano (7), siloxane (8). N-t-BOC (9) and benzyl ether (10) terminated macromolecules as shown in FIGS. 4 and 5. Formation of this series of cascades is supported by the simple off-resonance $^{13}C$ NMR spectra as depicted in FIG. 4 (6–8) and FIG. 5 (9 and 10). Dominate and anticipated key absorptions corresponding to the covalently attached 1→3 branched monomers, are observed for each recorded spectrum [e.g., (δ) 6; 172.7 $\underline{C}O$, 80.0 $\underline{C}(CH_3)$, 27.9 $\underline{C}H_3$: 7; 118.4 $\underline{C}N$, 69.8, 65.9 $\underline{C}H_2O\underline{C}H_2$, 18.8 $\underline{C}H_2CN$: 8; 63.6 $\underline{C}H_2O$, 26.0 C($\underline{C}H_3)_3$, 18.2 $\underline{C}(CH_3)_3$, −5.2 Si($\underline{C}H_3)_2$: 9; 156.5 $\underline{C}O$, 78.9 $\underline{C}(CH_3)_3$, 28.3 C($\underline{C}H_3)_3$: 10 138.6, 128.4, 127.6, 127.4 ($\underline{C}$, aryl), 72.8 ($\underline{C}H_2C_6H_5$), 71.0 ($CH_2\underline{C}H_2O$)]. Peaks attributed to the imine-based superstructure appear broadened and less intense [e.g., (δ) 6; 52.0 $\underline{C}H_2CH_2\underline{C}H_2$, $\underline{C}H_2CH_2CH_2\underline{C}H_2$, 51.0 $\underline{C}H_2CH_2CH_2NHCONH$] as expected (Table 1).

Table 1: $^{13}C$ NMR Data for New Compounds (subscripts denote absorptions arising from specified units)

6 δ 172.7 ($\underline{C}O$); 157.9 (NH$\underline{C}ONH$); 80.0 ($\underline{C}(CH_3)_3$); 56.0 ($\underline{C}_4°$); 52.1 ($\underline{C}H_2CH_2CH_2CH_2$, $\underline{C}H_2CH_2\underline{C}H_2$); 51.0 ($\underline{C}H_2CH_2CH_2NHCONH$); 37.8 ($\underline{C}H_2NHCONH$); 30.2, 29.5 ($\underline{C}H_2\underline{C}H_2CO_2$, $\underline{C}H_2\underline{C}H_2NHCONH$); 27.9 (C($\underline{C}H_3)_3$); 24.2 ($CH_2\underline{C}H_2\underline{C}H_2CH_2$, $CH_2\underline{C}H_2CH_2$): 7 δ 158.2 (NH$\underline{C}ONH$); 118.4 ($\underline{C}N$); 69.8, 65.9 ($\underline{C}H_2O\underline{C}H_2$); 58.9 ($\underline{C}_4°$); 52.0 ($\underline{C}H_2CH_2\underline{C}H_2$, $\underline{C}H_2CH_2CH_2\underline{C}H_2$); 51.0 ($\underline{C}H_2CH_2CH_2NHCONH$); 38.3 ($\underline{C}H_2NHCONH$); 29.6 ($CH_2\underline{C}H_2\underline{C}H_2CH_2$); 27.4 ($\underline{C}H_2\underline{C}H_2NHCONH$); 23.8 ($CH_2\underline{C}H_2CH_2$); 18.8 ($\underline{C}H_2CN$): 8 δ 158.2 (NH$\underline{C}ONH$); 63.6 ($\underline{C}H_2O$); 56.7 ($\underline{C}_4°$); 52.2 ($\underline{C}H_2CH_2\underline{C}H_2$, $\underline{C}H_2CH_2CH_2\underline{C}H_2$); 51.0 ($\underline{C}H_2CH_2CH_2NHCONH$); 38.0 ($\underline{C}H_2NHCONH$); 32.0 $\underline{C}H_2CH_2CH_2O$); 29.0 ($CH_2\underline{C}H_2\underline{C}H_2CH_2$); 26.9 ($\underline{C}H_2CH_2O$); 26.0 (C($\underline{C}H_3)_3$); 25.0 ($\underline{C}H_2CH_2NHCONH$); 24.2 ($CH_2\underline{C}H_2CH_2$); 18.2 ($\underline{C}(CH_3)_3$); −5.2 (Si($\underline{C}H_3)_2$): 9 δ 158.7 (NH$\underline{C}ONH$); 156.5 ($\underline{C}O$); 78.9 ($\underline{C}(CH_3)_3$); 57.0 ($\underline{C}_4°$); 52.4 ($\underline{C}H_2CH\underline{C}H_2$); ($\underline{C}_2CH_2CH_2$); 51.4 ($\underline{C}H_2CH_2CH_2NHCONH$); 41.2 ($CH_2\underline{C}H_2NH$); 37.9 $\underline{C}HNHCONH$); 33.3 ($\underline{C}H_2CH_2CH_2$); 29.8 ($\underline{C}H_2CH_2NHCONH$); 28.7 (C($\underline{C}H_3)_3$); 23.9 ($CH_2\underline{C}H_2CH_2$, $CH_2\underline{C}H_2\underline{C}H_2CH_2$): 10 δ 158.2 (NH$\underline{C}ONH$); 138.6 ($\underline{C}_1$ aryl); 128.4 ($\underline{C}_2$ aryl); 127.6 ($\underline{C}_3$ aryl); 127.4 ($\underline{C}_4$ aryl); 72.8 ($\underline{C}H_2C_6H_5$); 71.0 ($CH_2\underline{C}H_2O$); 56.9 ($\underline{C}_4°$); 52.3 ($\underline{C}H_2CH_2CH_2CH_2$, $\underline{C}H_2CH_2\underline{C}H_2$); 50.9 ( $CH_2CH_2CH_2NHCONH$); 37.7 ($CH_2NHCONH$); 32.1 ( $CH_2CH_2CH_2O$); 28.2 ($CH_2CH_2NHCONH$); 23.8 ($CH_2CH_2CH_2O$): 11 and 12 δ 172.8 ($CO_{[BA]}$); 157.8, 157.6 (NH $CONH_{[BA, Si, CN]}$); 118.3 ($CN$); 80.1 ($C(CH_3)_{3[BA]}$); 69.9, 65.8 ($CH_2OCH_{2[CN]}$); 63.5 ($CH_2O_{[Si]}$); 58.9 ($C_{4°[CN]}$); 56.0 ($C_{4°[BA]}$); 51.5 ($CH_2CH_2CH_{2[DSM]}$, $CH_2CH_2CH_{2[DSM]}$, $CH_2CH_2CH_2NHCONH_{[DSM]}$); 38.8

Table 1 (continued)

($CH_2NHCONH_{[DSM]}$); 32.0 ($CH_2CH_2O_{[Si]}$); 30.3, 29.6, 28.0 ($CH_2CH_2CO_2$, $C(CH_3)_{3[BA]}$); 25.9 ($C(CH_3)_{3[Si]}$); 24.2 ($CH_2CH_{2[DSM]}$); 18.7 ($CH_2CN_{[CN]}$); 18.2 ($C(CH_3)_{3[Si]}$); −5.3 ($Si(CH_3)_2$); 13 δ 158.5 ($NHCONH_{[N-t-BOC, BE]}$); 156.4 ( $CO_{[N-t-BOC]}$); 138.7 ($C_1$ aryl$_{[BE]}$); 128.6 ($C_2$ aryl$_{[BE]}$); 127.8 ($C_{3,4}$ aryl$_{[BE]}$); 78.9 ($C(CH_3)_{3[N-t-BOC]}$); 72.9 ( $CH_2C_6H_{5[BE]}$); 71.0 ($CH_2CHO_{[BE]}$); 57.0 ($C_{4°[N-t-BOC, BE]}$); 52.4 ($CH_2CH_2CH_2CH_{2[DSM]}$, $CH_2CH_2CH_{2[DMS]}$); 51.4 ( $CH_2CH_2CH_2NHCONH_{[DSM]}$); 41.2 ($CH_2$ $CH_2NH_{[N-t-BOC]}$); 37.9 ($CH_2NHCONH_{[DSM]}$); 33.2 ( $CH_2CH_2CH_{2[N-t-BOC]}$); 32.3 ($CH_2CH_2CH_2O_{[BE]}$); 28.8 (C( $CH_3)_{3[N-t-BOC]}$); 23.9 ($CH_2CH_2CH_{2[N-t-BOC, BE]}$, $CH_2CH_2$ $CH_{2[DSM]}$): 14 δ 173.1 ($CO_{[BA]}$); 158.2 (NH $CONH_{[BA, CN, N-t-BOC, BE]}$); 156.5 ($CO_{[N-t-BOC]}$); 138.7 ($C_1$ aryl$_{[BE]}$); 128.5 ($C_2$ aryl$_{[BE]}$); 127.7 ($C_{3,4}$ aryl$_{[BE]}$); 118.7 ( $CN_{[CN]}$); 80.5 ($C(CH_3)_{3[BA]}$) 78.9 ($C(CH_3)_{3[N-t-BOC]}$); 72.9 ( $CH_2C_6H_{5[BE]}$); 71.1 ($CH_2CH_2O_{[BE]}$); 70.1, 66.0 ($CH_2O$ $CH_{2[CN]}$); 57.1, 56.2 ($C_{4°[BA, CN, N-t-BOC, BE]}$); 51.4 ( $CH_2CH_2CH_{2[DSM]}$, $CH_2CH_2CH_2CH_{2[DSM]}$, $CH2CH_2CH_2NHCONH_{[DSM]}$); 41.1 $CH_2CH_2CN_{[CN]}$); 38.3 ($CH_2NHCONH_{[DSM]}$); 33.2 ($CH_2CH_2CH_{2[N-t-BOC]}$, $CH_2CH_2CH_2O_{[BE]}$); 32.2, 29.9 ($CH_2CH_2CO_{2[BA]}$); 28.7, 28.3 ($C(CH_3)_{3[BA, N-t-BOC]}$); 23.8 ($CH_2CH_2CH_{2[N-t-BOC, BE]}$, $CH_2CH_2CH_2CH_{2[DSM]}$); 18.9 ($CH_2CN_{[CN]}$).

Example 2

Further potential to exploit the isocyanate-based monomer connectivity was subsequently examined by treatment of the 32-PPI dendrimer with monomer mixtures consisting of a total of 32 quivalents of triester (1), trinitrile (2), and trisiloxane (3). Specifically, tier formation using mixtures comprised of the appropraite equivalents of the building blocks (1), (2), and (3) [(0.5, 0.1, and 0.4) or (0.7, 0.15, and 0.15), respectively] afforded the corresponding 'combinatorial-based' dendrimers (11) and (12) (FIG. 3).

Evidence for the formation of these chromatographically purified, peripherally heterogeneous dendrimers includes the spectra ($^{13}C$ NMR) observation of all pertinent signals exhibited in the spectra of the analogous, peripherally homogeneous macromolecules (6–8). More specifically, the spectra of each mixed-surface cascade exhibits signals at 172.8, 118.3, 80.1, 63.5, 51.5, 18.7, and −5.3 ppm corresponding to the $CO_{[BA]}$, $CN$, $C(CH_3)_{3[BA]}$, $CH_2O_{[Si]}$, $CH_2CH_{2[DSM]}$, $CH_2CN$, $Si(CH_3)_2$ moieties, respectively. The observed low intensity and slightly broadened appearance of the absorptions at 157.8 and 157.6 ppm ($NHCONH_{BA, Si, CN}$) suggest a relatively rigid surface promoted by urea-based $H$-bonding and termini crowding.

Example 3

Figure 6:
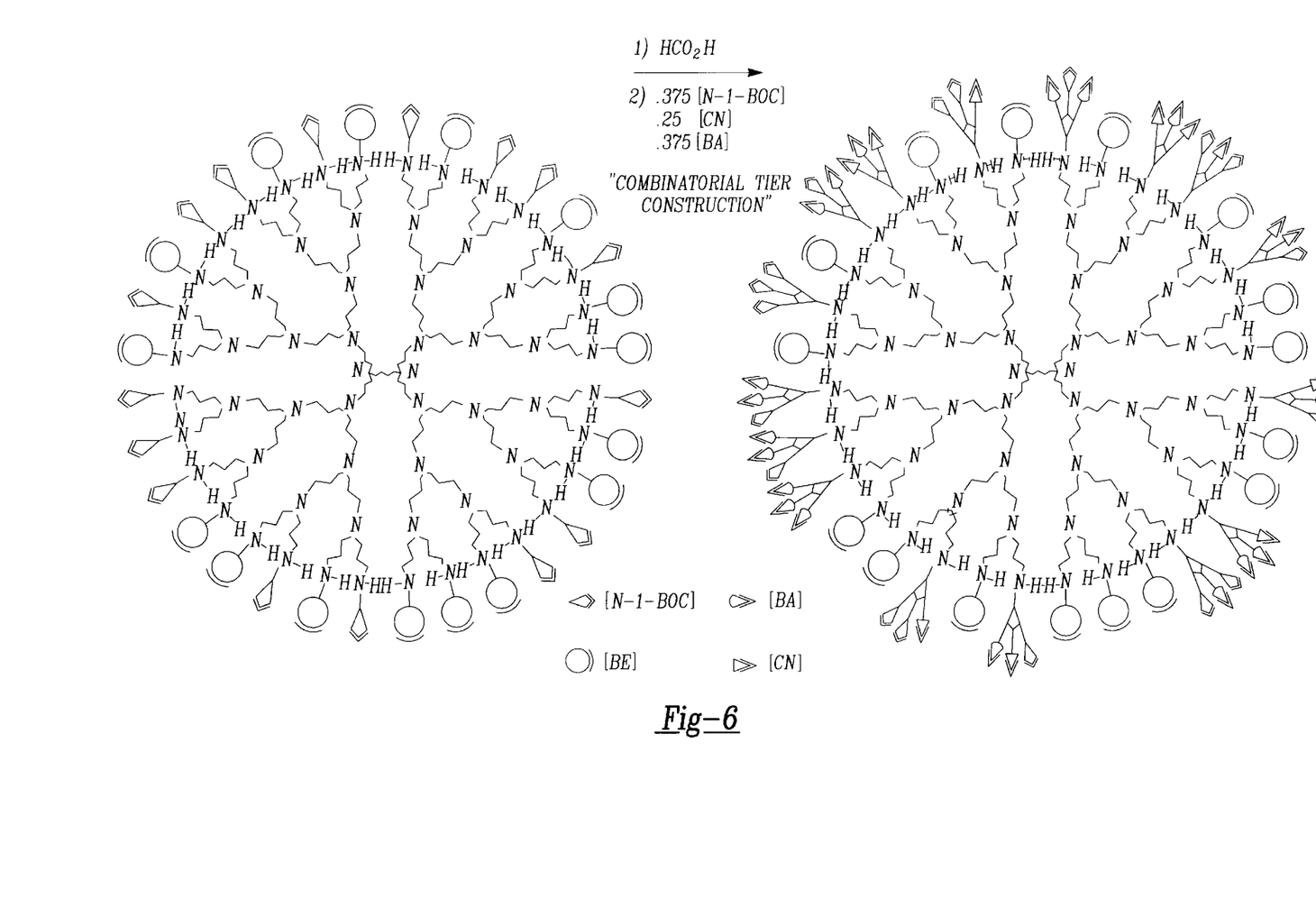
FIG. 6 shows a construction of a "double-layered" combinatorial-based dendrimer.

FIG. 6 illustrates the concept of combinatorial growth as it relates to the construction of the multifarious surfaced dendrimers (e.g., treatment of the DSM 32 PPI dendrimer with a mixture of 16 equivalents each of the N-t-BOC (4) and benzyl ether (5) monomers in refluxing dichloromethane afforded the hetereogeneous macromolecule 13. Following isolation and purifification, the structure of the new heterdendrimer 13 was conffirmed by $^{13}C$ NMR (FIG. 5, Table 1) which contained the relevant signals exhibited in the spectra of both the corresponding homogeneous macromolecules (9 and 10). Principal signals were observed at (ppm) 138.7, 128.6, 127.8 ($Caryl)_{[BE]}$, 78.9 $C(CH_3)_{3[N-t-Boc]}$.

Removal of the BOC groups ($HCO_2H$) and subsequent reaction of the free amines with a mixture of isocyanate monomers (1), (2) and (4) [equivalent: 0.375, 0.25, 0.375, respectively] yielded the functionally diverse dendritic material 14. Structure verification of the unsymmetrical dendrimer 14 was supported by $^{13}C$ NMR (FIG. 5) which revealed the expected peaks at 173.1 $CO_{[BA]}$ 156.5 $CO_{[N-t-Boc]}$, 138.7, 128.5, 127.7 $Caryl_{[BE]}$, 118.7 $CN$, 80.5 $C(CH_3)_{3[BA]}$, 78.9 $C(CH_3)_{3[N-t-BOC]}$, 72.9 $CH_2C_6H_{5[BE]}$, 28.7, 28.3 $C(CH_3)_{3[N-t-BOC,BA]}$, 18.9 $CH_2CN_{[CN]}$. Analogously, similar signals are observed in the homogeneous macromolecules (6), (7), (9) and (10). Higher generation combinatorial materials can easily be constructed by further selective, functional group deprotection followed by treatment with any mixture of compatible isocyanate-based monomers.

To demonstrate the potential to effect dendrimer properties, such as conformational changes, based on surface group modification, the polyamine dendrimer afforded by liberation of the amine moieties on dendrimer 13 (50:50 mixture of N-t-BOC and BE) displayed amphiphlic behavior. For example, it is highly soluble in MeOH and only partially soluble in both $H_2O$ and $CHCl_3$. Key $^{13}C$ NMR signals arising from either the amine- or benzyl ether-based arms collapse and broaden in the deuterated solvents $CDCl_3$ and $D_2O$, respectively. This can be rationalized by considering that surface groups with termini that favor solvation are extended and freely rotate while groups with unfavorable solvent interactions are contracted and folded back into the molecular superstructure where less freedom of movement is afforded. Gitsov and Frechet, [1993 and 1996] have observed analogous behavior upon attachment of dendritic wedges to polyethylene glycol star polymers. Modification of this behavior can be achieved by altering the ratio of the functional groups on the dendrimer surface. For example, a 75:25 mixture of amine and benzyl ether moieties is completely miscible in $H_2O$ and insoluble in $CHCl_3$.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically describe.

REFERENCES

Carell et al., 1995, "New promise in combinatorial chemistry: synthesis, characterization, and screening of small-molecule libraries in solution", Chem. Biol., 2:171–183

Carell et al., 1994, "Novel Procedure for Synthesis of Libraries Containing Small Organic Colecules", Angew. Chem., Int. Ed. Engl., 33(2):2059–2061 deBrabander-van den Berg and Meijer, 1993a, "Poly (propylene imine) Dendrimers: Large-Scale Synthesis by Hetereogeneously Catalyzed Hydrogenations", Angew Chem., Int. Ed. Engl., 32:1308

Domingeuz et al., 1961, "Simple Preparation of a Very Active Rancy Nickel Catalyst", J. Org. Chem. 26:1625

Gitsov and Frechet, 1996, "Stimuli-Responsive Hybrid Macromolecules: Novel Amphiphilic Star Copolymers with Dendritic Groups at the Periphery", *J. Org. Chem.*, 118:3785–3786

Gitsov and Frechet, 1993, "Solution and Solid-State Properties of Hybrid Linear-Dendritic Block Copolymers", *Macromolecules*, 26:6536–6546

Newkome and Weis, 1996, "Di-tert-Butyl 4-[2-tert-BUTOXYCARBONYL) ETHYL]-4-AMINOHEPTANEDICARBOXYLATE", *Org. Prep. Proc. Int.*, 28:485–488

Plattner et al., 1972, "Synthesis of Some DE and CDE Ring Analogs of Camptothecin", *J. Am. Chem. Soc.*, 94:8613–8615 van Gendersen et al., 1994, "Observing Individual Generations in Poly(propyleneimine) Dendrimers with Natural Abundance $^{15}$N-NMR spectroscopy" *Recl. Trav. Chim. Pays-Bas.*, 113:573–574

Wörner, and Mülhaupt., 1993, "Polynitrile- and Polyamine-Functional Poly(trimethylene imine) Dendrimers", *Angew Chem., Int. Ed. Engl.*, 32(9):1306–1308

Xiang et al., 1995, "Combinatorial Approach to Materials Discovery", *Science*, 268:1738–1740

What is claimed is:

1. An amphiphlic heterodendrimer consisting of a core molecule and a mixture of branching arms extending therefrom including a mixture of branched monomers dendrimerized through an isocyanate reaction.

2. An amphiphilic heterodendrimer consisting of a core molecule and flexible arms branching therefrom to rotatable termini defining an outer surface, said termini being differentially soluble whereby termini soluble in an external mixture are extended from said core and rotatable, while termini not soluble in the external mixture are contracted and folded towards said core and are less rotatable.

3. An amphiphilic heterodendrimer as in claim 2 including a mixture of terminal groups selected from the group consisting of amines, benzyl ether, carboxyls, alcohols, siloxanes, esters, acetates, cyanates, thiols, sulfides, sulfates, phosphines, phosphates, ammonium, amides, amidines, nitroxyl, nitrate, nitraso, alkyl, alkene, alkyne, aryl, and araalkyl.

* * * * *

UNITED STATES PATENT AND TRADEMARK OFFICE
CERTIFICATE OF CORRECTION

PATENT NO : 5,886,127
DATED : March 23, 1999
INVENTOR(S): George R. Newkome, Charles N. Moorefield It is certified that error appears in the above-indentified patent and that said Letters Patent is hereby corrected as shown below:

On the title page, insert:

The term of this patent shall not extend beyond the expiration date of Pat. No.: 5,886,126.

Signed and Sealed this

Twenty-eighth Day of September, 1999

*Attest:*

Q. TODD DICKINSON

*Attesting Officer*     *Acting Commissioner of Patents and Trademarks*